(12) United States Patent
Bevot et al.

(10) Patent No.: US 9,347,903 B2
(45) Date of Patent: May 24, 2016

(54) METHOD FOR DETECTING THE TYPE OF LAMBDA PROBES

(75) Inventors: Claudius Bevot, Stuttgart (DE); Rolf Reischl, Stuttgart (DE); Thomas Classen, Stuttgart (DE); Benjamin Sillmann, Moehringen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 570 days.

(21) Appl. No.: 13/702,755

(22) PCT Filed: May 18, 2011

(86) PCT No.: PCT/EP2011/058045
§ 371 (c)(1),
(2), (4) Date: Apr. 10, 2013

(87) PCT Pub. No.: WO2011/154228
PCT Pub. Date: Dec. 15, 2011

(65) Prior Publication Data
US 2013/0186169 A1    Jul. 25, 2013

(30) Foreign Application Priority Data
Jun. 8, 2010 (DE) .................. 10 2010 029 776

(51) Int. Cl.
*G01N 21/00* (2006.01)
*G01N 27/04* (2006.01)
*G01N 27/406* (2006.01)
*G01N 27/417* (2006.01)

(52) U.S. Cl.
CPC .......... *G01N 27/046* (2013.01); *G01N 27/4065* (2013.01); *G01N 27/4175* (2013.01)

(58) Field of Classification Search
CPC . G01N 27/00; G01N 27/046; G01N 27/4065; G01N 27/4175
See application file for complete search history.

(56) References Cited

U.S. PATENT DOCUMENTS 4,666,566 A * 5/1987 Mizutani ............ G01N 27/4065
204/410
6,034,610 A * 3/2000 Schnaibel ............... F02B 39/16
123/679

(Continued)

FOREIGN PATENT DOCUMENTS

DE    102006014266      * 5/2006
DE    10 2007 009 157      8/2008

(Continued)

OTHER PUBLICATIONS

International Search Report, PCT International Application No. PCT/EP2011/058045, dated Aug. 4, 2011.

*Primary Examiner* — John Fitzgerald
*Assistant Examiner* — Truong Phan
(74) *Attorney, Agent, or Firm* — Norton Rose Fulbright US LLP

(57) ABSTRACT

Methods for detecting the type of lambda probes having at least two electrodes disposed on and/or in a solid electrolyte, of which at least one electrode is separated from a gas mixture by a diffusion barrier, and a pump current Ip being applied to at least one of the electrodes. Either the internal resistance of the lambda probe between the electrodes is determined and the type of probe is inferred on the basis of this resistance, or currents are impressed between the electrodes and the type of probe is inferred based on the voltages or resistance ratios thereby resulting.

6 Claims, 2 Drawing Sheets

(56) References Cited

U.S. PATENT DOCUMENTS

| | | | | |
|---|---|---|---|---|
| 6,073,083 A | * | 6/2000 | Schnaibel | G01N 27/4065 324/691 |
| 2005/0000832 A1 | * | 1/2005 | Holoch | G01N 27/419 205/782 |
| 2005/0173265 A1 | * | 8/2005 | Stahl | F01N 3/0814 205/783.5 |
| 2006/0105638 A1 | * | 5/2006 | Pade | H01R 13/4362 439/752 |
| 2007/0261475 A1 | * | 11/2007 | Allmendinger | G01N 27/419 73/31.01 |
| 2009/0095627 A1 | * | 4/2009 | Diehl | G01N 27/419 204/425 |
| 2009/0107839 A1 | * | 4/2009 | Scheffel et al. | 204/406 |
| 2010/0073017 A1 | * | 3/2010 | Bevot | G01N 27/4067 324/703 |
| 2011/0093184 A1 | * | 4/2011 | Wagner | G01N 27/4065 701/103 |
| 2012/0167656 A1 | | 7/2012 | Verdier et al. | |

FOREIGN PATENT DOCUMENTS

| | | | |
|---|---|---|---|
| DE | 10 2007 020 970 | | 11/2008 |
| DE | 10 2007 057 707 | | 6/2009 |
| DE | 102009027378 | * | 7/2009 |
| DE | 10 2009 029 690 | | 3/2010 |
| WO | WO 2009/130266 | | 10/2009 |
| WO | WO 2009/135862 | | 11/2009 |
| WO | WO 2011/000853 | | 1/2011 |

* cited by examiner

METHOD FOR DETECTING THE TYPE OF LAMBDA PROBES

FIELD OF THE INVENTION

The present invention relates to a method for detecting the type of lambda probes. The present invention also concerns a computer program and a computer-program product which are suitable for implementing the method.

BACKGROUND INFORMATION

A great variety of probes are used in today's type of vehicle construction. First of all, there are probes which have two pump electrodes disposed on a solid electrolyte, as described, for example, in German Patent Application No. DE 10 2007 009 157 A1 or in German Patent Application No. DE 10 2007 020 970 A1. Moreover, there are also what are termed broadband lambda probes having two cells, as described, for example, in German Patent Application No. DE 10 2007 057 707 A1. These probes are used to measure the concentration of a gas component in the exhaust gas of the internal combustion engine. Broadband lambda probes are made generally of a combination of a conventional concentration probe (Nernst probe) acting as a galvanic cell, as well as a limit-current cell or pump cell. A voltage is applied from outside to the pump cell, which is of the same kind as a customary concentration cell. If the voltage is great enough, what is termed a limiting current ensues, which is proportional to the difference in the oxygen concentration on both sides of the probe. Oxygen atoms are transported—as a function of polarity—with the current values. Owing to an electronic regulating circuit, the pump cell always supplies exactly enough oxygen from the exhaust gas via a very narrow diffusion gap to the concentration probe, so that the condition $\lambda=1$ prevails at it. In response to excess air in the exhaust gas (lean-combustion range), oxygen is pumped away. In the case of low residual oxygen content in the exhaust gas (rich-mixture range), oxygen is supplied by reversing the pump voltage. The specific pump current forms the output signal. The output-signal line of such broadband lambda probes is connected to the engine control unit.

If, for example, a lambda probe is now replaced, then purely as a matter of principle, a probe of the same type must always be used. An exchange of lambda probes is not readily possible, since their output signals cannot be processed properly in the control unit.

SUMMARY

An object of the present invention is to provide a method for characterizing and detecting probes from various manufacturers and of different types, whose output signals are able to be processed.

In accordance with an example embodiment of the present invention, a method is provided for detecting the type of lambda probes of the sort described at the outset, in the manner that the internal resistance of the lambda probe between the electrodes is determined at at least one predefined operating temperature of the probe, and the type of probe is inferred on the basis of the value of the internal resistance.

Thus, in one advantageous embodiment of the example method, a further variable characterizing the probe is determined, and the type of probe is inferred based on the value of the internal resistance and the at least one further variable characterizing the probe. In this development, two items of information are utilized. By assessing these two items of information, namely, the probe signal and the internal resistance, the type of probe is inferred.

Highly diverse variables may come into consideration as a further variable characterizing the probe.

A first advantageous refinement provides that, as the at least one further variable characterizing the probe, the probe signal as a result of an additionally impressed pump current is determined, and the type of probe is inferred by comparing the probe signal to the internal resistance.

In another development of the present invention, as at least one further variable characterizing the probe, the internal resistance between a further electrode and one of the two other electrodes at at least one predefined operating temperature of the probe is ascertained, and the type of probe is inferred based on the ratio of the internal resistances. Thus, for example, the internal resistance between an inner pump electrode and an outer pump electrode may be ascertained at at least one predefined operating temperature of the probe, and the type of probe may be inferred from the ratio of the internal resistances.

According to a further advantageous development, it may be provided that, in addition to the internal resistance and the internal-resistance ratio, respectively, a trimming resistance is determined between an outer pump electrode exposed to the gas mixture, and a measuring electrode, and the type of probe is inferred based on the trimming resistance in conjunction with the internal resistance or the ratio of the internal resistances. It may be that purely as a matter of principle, the determination of the resistance or the resistance ratio is sufficient; however, the additional measurement of the trimming resistance, also know as balancing resistance, code resistance or rank resistance, represents an additional possibility for precisely determining the type of probe.

In addition to or as an alternative to determining the internal resistance or the internal-resistance ratios, variables may also be used which are linked directly or indirectly to the internal resistance or to the internal-resistance ratios and/or the capacitances of the probe.

In accordance with an example embodiment of the present invention, a method is provided for detecting the type of broadband lambda probes which have a pump cell and a Nernst cell, the method being characterized in that a short circuit is produced between the outer pump electrode and an inner pump electrode, and the voltage thereby resulting between a reference electrode and the inner pump electrode is measured, and the type of probe is inferred from the magnitude of the change in voltage. This method is usable especially during the operation of the probe, but may also be used particularly when the probes to be identified do not differ with respect to their internal-resistance ratio and with respect to their trimming resistance in a manner sufficiently clear-cut that it is possible to determine the probe.

In accordance with an example embodiment of the present invention, a method is provided for detecting the type of broadband lambda probes that have a pump cell and a Nernst cell, the method being characterized in that, at a regulated pump-current value necessary for the proper operation of the broadband lambda probe, an adjustable, additional pump-current amount is impressed between an outer pump electrode and an inner pump electrode, and the change in voltage between a reference electrode and the inner pump electrode is measured, and the type of probe is inferred from this change in voltage. This design approach is usable especially when short-circuiting between the outer pump electrode and the inner pump electrode is not possible for reasons of circuit engineering or is not provided.

In a refinement of the two example methods described above, the measurement is performed cyclically over the operational duration of the probe, and the aging of the probe is inferred based on the change in voltage between the reference electrode and the inner pump electrode over the operating time. An additional statement about the electrode aging and the aging of the zirconium oxide which forms the electrolyte of the probe is thereby possible.

Purely as a matter of principle, the aforementioned methods of the present invention may be implemented as a computer program which runs in a control-unit program, e.g., as a subprogram. The program code is advantageously stored in a computer-program product, e.g., a CD-ROM, a memory stick or the like, and in this way, retrofitting of the method(s) in existing control units is easily possible without additional hardware expenditure.

BRIEF DESCRIPTION OF THE DRAWINGS

Exemplary embodiments of the present invention are shown in the figures and explained in greater detail below.

DETAILED DESCRIPTION OF EXAMPLE EMBODIMENTS

Gas sensors of various kinds are used to determine the gas composition in the exhaust gas of internal combustion engines, particularly internal combustion engines in motor vehicles. In addition to oxygen-concentration sensors, so-called voltage-jump sensors or lambda probes, what are termed broadband lambda probes are used especially for the wide lean-combustion range. They are made generally of a combination of a conventional concentration probe acting as galvanic cell, what is known as a Nernst probe, as well as a limit-current cell or "pump" cell.

The method of the present invention is described in the following by way of example in connection with such a broadband lambda probe. At this point, it should be mentioned and stressed that the present invention is not limited to such broadband lambda probes, but rather, purely as a matter of principle, is also usable in the case of probes which are made up of just one cell and in which the two electrodes are situated on the upper side of an electrolyte, for example, as described, e.g., in German Patent Application No. DE 10 2007 020 970 A1.

Figure 1:
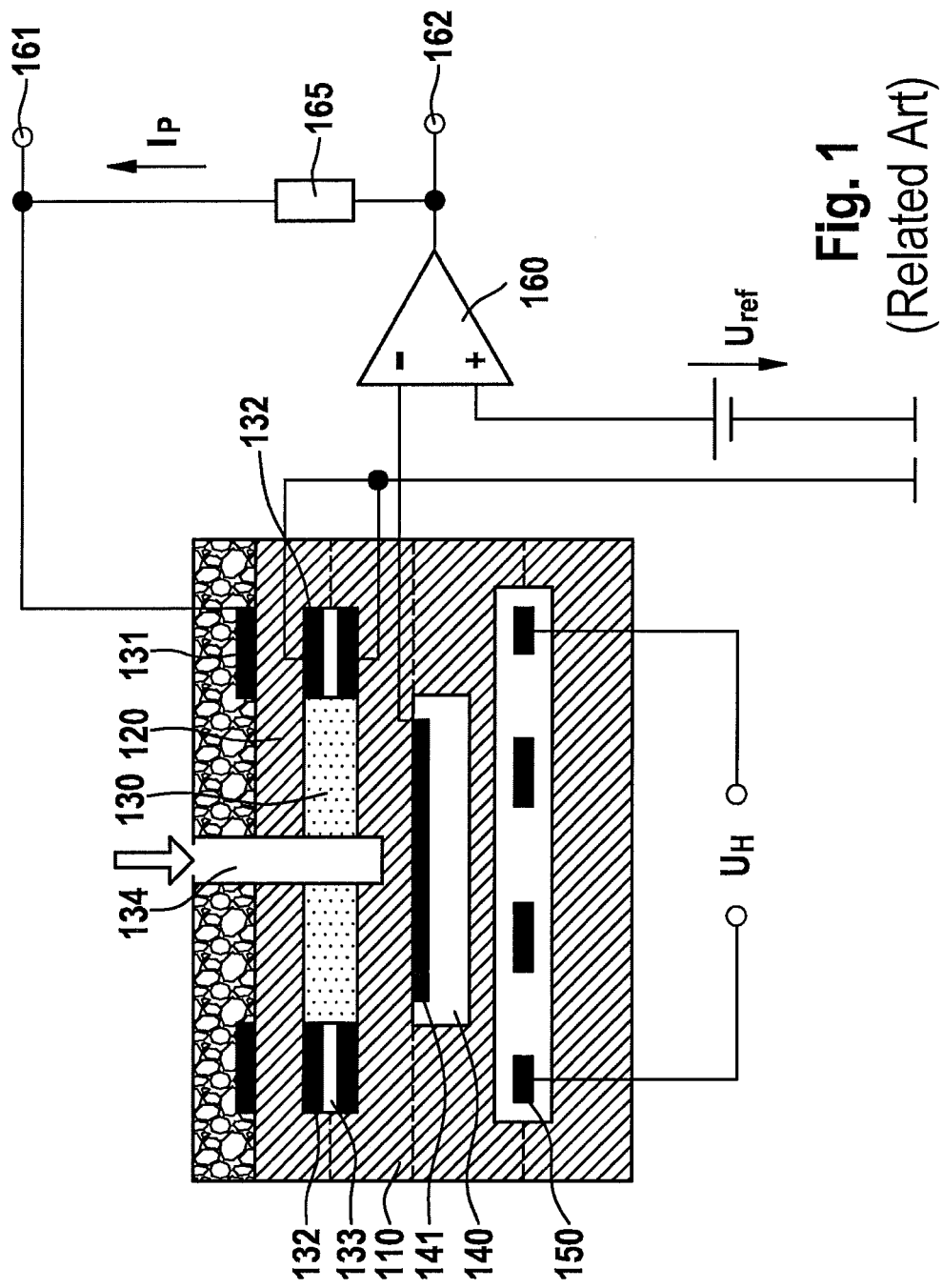
FIG. 1 shows schematically a conventional broadband lambda probe for explaining its functional principle.

FIG. 1 shows schematically the construction of a broadband lambda probe. It has a Nernst concentration cell 110 and an oxygen pump cell 120, oxygen pump cell 120 being formed by an outer pump electrode 131 and an inner pump electrode 132. Outer pump electrode 131 is exposed to exhaust gas A, and inner, ring-shaped pump electrode 132 is disposed in a cavity 133 that is in communication with exhaust gas A via a channel 134 and a diffusion gap in which a diffusion barrier 130 is located. Nernst cell 110 is formed by inner pump electrode 132 and a reference electrode 141 which is situated in a reference air channel 140. The probe is brought to operating temperature by a heater 150, to which a heating voltage $U_H$ is applied. A regulating circuit 160 formed, e.g., by an operational amplifier, at whose non-inverting input a reference voltage of, in particular, 450 mV is applied, and at whose inverting input, the output signal of reference electrode 141 is applied, generates a pump current $I_P$, which is applied to outer pump electrode 131. Inner pump electrode 132 is connected to ground. Pump current $I_P$ is able to be tapped off with the aid of terminals 161, 162 across a resistor 165. It forms a measure for the oxygen concentration, as described briefly below.

A voltage is applied to pump cell 120. If the voltage is great enough, a "limit current" is obtained, which is proportional to the difference in the oxygen concentration on both sides of the probe. Oxygen atoms are transported—as a function of polarity—with the current. Owing to regulating circuit 160, pump cell 120 always supplies exactly enough oxygen from exhaust gas A via the narrow diffusion gap and diffusion barrier 130 to concentration probe 110, so that the condition $\lambda=1$ prevails at it. In response to excess air in the exhaust gas (lean-combustion range), oxygen is pumped away. In the case of low residual oxygen content in the exhaust gas (rich-mixture range), oxygen is supplied by reversing the pump voltage. The pump current, which is able to be tapped off via terminals 161, 162, forms the output signal; it represents a measure of the oxygen concentration, and therefore of the lambda value.

Figure 2:
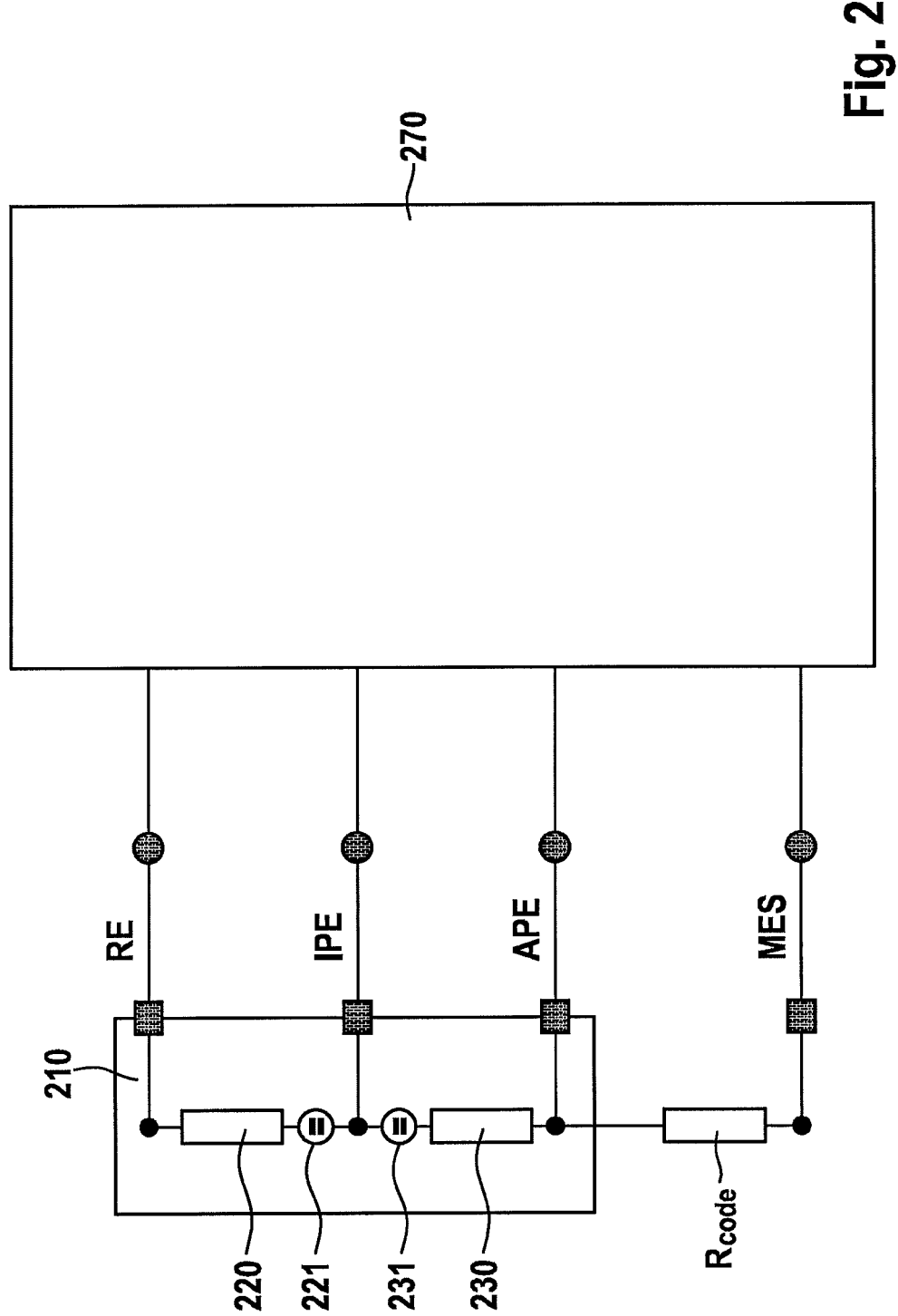
FIG. 2 shows schematically the internal resistances of the pump cell, the Nernst cell as well as the trimming resistor to explain the example methods of the present invention.

Located in the plug connector of such broadband lambda probes are now trimming resistors, also called balancing-, code- or rank resistors, which, for instance, are disposed in parallel with respect to resistor 165. They are used to adapt or calibrate the broadband lambda probe. The broadband lambda probe, which is represented schematically in FIG. 2 by an equivalent circuit diagram 210, includes internal resistor 220 and a fictitious voltage source 221 of the Nernst cell (denoted by 110 in FIG. 1) and internal resistor 230 and fictitious voltage source 231 of the pump cell (denoted by 120 in FIG. 1). Internal resistor 220 of Nernst cell 110 is able to be tapped off via terminals RE and IPE, "RE" standing for reference electrode (denoted by 141 in FIG. 1) and "IPE" standing for inner pump electrode (denoted by 132 in FIG. 1). Internal resistor 230 of pump cell 120 is able to be tapped off via terminals IPE and APE, "APE" standing for outer pump electrode (denoted by 131 in FIG. 1). Disposed outside of probe 210 is a trimming resistor $R_{code}$, also called balancing-, trimming- or rank resistor, that is able to be tapped off via a measuring terminal MES. The respective output-signal lines are connected to a corresponding circuit module 217, also denoted as lambda-probe evaluation module. With the aid of this module, it is possible to measure the ohmic resistances both between the reference electrode and the inner pump electrode (resistor 220), and between the inner pump electrode and outer pump electrode (resistor 230), as well as between the outer pump electrode and the measuring terminal MES (resistor $R_{code}$) and to evaluate these resistances. The ratio of resistor 220 to resistor 230 represents a characteristic property of the probe. This ratio is constant over a temperature range from approximately 550° C. to 800° C., thus, over a specific predefined temperature range. In the case of a probe of a first type, this ratio may be 1:1, for example. The value of trimming resistor $R_{code}$ is 4 kOhm, for instance. In the case of a probe of another type, for example, the ratio of resistor 220 to resistor 230 is 4.2:1 over the temperature range of 550° C. to 800° C. and the maximum trimming resistor $R_{code}$ is less than 150 Ohm. With the aid of module 170, it is possible to precisely determine the resistances and therefore the resistance ratios, and thus to draw conclusions about the probe used.

If the probes to be identified do not differ clearly with regard to the internal-resistance ratios and the trimming resistance, by measuring the "distance" of the reference electrode to the outer pump electrode and the inner pump electrode, an additional feature, so to speak, may be utilized for identifying the probe, which is determined by the inner construction of the probe.

To that end, in another refinement of the method according to the present invention, the voltage between outer pump electrode APE and inner pump electrode IPE is purposefully manipulated, and this "distance" is determined based on a measurement of the reaction at reference electrode RE. Distance here is understood to be a length which, for instance, may be indicated in millimeters. Namely, due to the internal probe construction, the electrodes at the inner pump electrode and the reference electrode have different distances relative to each other. Purely as a matter of principle, the manipulation may be carried out in two ways. In a first refinement of the method according to the present invention, the voltage between the outer pump electrode and the inner pump electrode is forced by the evaluation circuit to 0 V, which corresponds to a short circuit between the two lines of outer pump electrode APE and inner pump electrode IPE. Owing to this short circuit, the voltage between reference electrode RE and inner pump electrode IPE changes. This change in voltage is able to be measured. The magnitude of the change in voltage is characteristic for the respective type of probe.

If, because of reasons of circuit engineering, short-circuiting is not possible or is not provided, then an alternative design approach of the present invention allows for the following method. On the basis of the last regulated pump-current value, which corresponds to a pump current for the proper operation of the broadband lambda probe, an adjustable and additional pump-current amount is impressed on pump cell 120, i.e., on inner pump electrode IPE and outer pump electrode APE, and the change in voltage between reference electrode RE and inner pump electrode IPE is measured. The voltage between reference electrode RE and inner pump electrode IPE, which in the normal case is regulated to a constant value of 450 mV, then increases or decreases by a characteristic amount, depending on the polarity of the additional pump-current amount. This increase or decrease of the voltage in turn represents a possibility for determining the type of probe, since each probe is assigned a characteristic amount. If this measurement is performed cyclically over the operational life of the probe, e.g., in each driving cycle after starting the engine or in the after run, then a conclusion may be drawn about the aging of the probe based on the change in the voltage swing between reference electrode RE and inner pump electrode IPE over time.

The alternatives described for the example method according to the present invention may be implemented, for example, as a computer program on a computing device, particularly control unit 170, and may run there. The program code may be stored in a machine-readable medium, e.g., a CD-ROM, a DVD-ROM, a memory stick or the like, which control unit 170 is able to read.

What is claimed is:

1. A method for detecting a type of lambda probe having at least two electrodes disposed at least one of on and in a solid electrolyte, of which at least one electrode is separated from a gas mixture by at least one diffusion barrier, and a pump current being applied to at least one of the electrodes, the method comprising:
   determining a first internal resistance of the lambda probe between the at least two electrodes at at least one predefined operating temperature of the probe; and
   determining the type of lambda probe based on a value of the first internal resistance and at least one further variable characterizing the type of lambda probe;
   wherein an additional pump-current amount is impressed between an outer pump electrode and an inner pump electrode in addition to a regulated pump-current value necessary for the proper operation of the lambda probe, and wherein a probe signal as the result of the additionally impressed pump-current is determined as the at least one further variable characterizing the type of lambda probe.

2. A method for detecting a type of lambda probe having at least two electrodes disposed at least one of on and in a solid electrolyte, of which at least one electrode is separated from a gas mixture by at least one diffusion barrier, and a pump current being applied to at least one of the electrodes, the method comprising:
   determining a first internal resistance of the lambda probe between the at least two electrodes at at least one predefined operating temperature of the probe; and
   determining the type of lambda probe based on a value of the first internal resistance and at least one further variable characterizing the type of lambda probe;
   wherein as the at least one further variable characterizing the type of lambda probe, a second internal resistance between a further electrode and one of the at least two electrodes of the lambda probe at at least one predefined operating temperature of the probe is ascertained, and the type of lambda probe is determined based on a ratio of the first and second internal resistances.

3. A method for detecting a type of lambda probe having at least two electrodes disposed at least one of on and in a solid electrolyte, of which at least one electrode is separated from a gas mixture by at least one diffusion barrier, and a pump current being applied to at least one of the electrodes, the method comprising:
   producing a short circuit between an outer pump electrode and an inner pump electrode, and measuring a voltage thereby resulting between a reference electrode and the inner pump electrode; and
   determining the type of lambda probe from a magnitude of a change in voltage.

4. A non-transitory, computer-readable storage medium storing a computer program for detecting a type of lambda probe having at least two electrodes disposed at least one of on and in a solid electrolyte, of which at least one electrode is separated from a gas mixture by at least one diffusive barrier, and a pump current being applied to at least one of the electrodes, the program code, when executed by a control unit of a vehicle, causing the control unit to perform the steps of:
   determining a first internal resistance of the lambda probe between the at least two electrodes at at least one predefined operating temperature of the probe; and
   determining the type of lambda probe based on a value of the first internal resistance and at least one further variable characterizing the type of lambda probe;
   wherein an additional pump-current amount is impressed between an outer pump electrode and an inner pump electrode in addition to a regulated pump-current value necessary for the proper operation of the lambda probe, and wherein a probe signal as the result of the additionally impressed pump-current is determined as the at least one further variable characterizing the type of lambda probe.

5. A method for detecting a type of lambda probe having at least two electrodes disposed at least one of on and in a solid electrolyte, of which at least one electrode is separated from a gas mixture by at least one diffusion barrier, and a pump current being applied to at least one of the electrodes, the method comprising:

impressing an adjustable, additional pump-current amount between an outer pump electrode and an inner pump electrode in addition to a regulated pump-current value necessary for the proper operation of the lambda probe;

measuring a change in voltage between a reference electrode and the inner pump electrode; and determining the type of lambda probe from the change in voltage.

6. The method as recited in claim 5, wherein the measurement is performed cyclically over an operational duration of the probe, and an aging of the probe is determined based on the change in voltage between the reference electrode and the inner pump electrode over the operating time.

\* \* \* \* \*